(12) United States Patent
Weaver et al.

(10) Patent No.: US 8,187,234 B2
(45) Date of Patent: May 29, 2012

(54) PRESSURE ACTIVATED SAFETY VALVE WITH ANTI-ADHERENT COATING

(75) Inventors: Karla Weaver, Framingham, MA (US); Paul DiCarlo, Middleboro, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 1680 days.

(21) Appl. No.: 10/768,571

(22) Filed: Jan. 29, 2004

(65) Prior Publication Data

US 2005/0171489 A1 Aug. 4, 2005

(51) Int. Cl.
*A61M 5/00* (2006.01)
(52) U.S. Cl. .................................. 604/247; 604/265
(58) Field of Classification Search ............ 604/9, 30, 604/93.01, 236, 244–247, 265, 167.01–167.06, 604/537; 623/1.43
See application file for complete search history.

(56) References Cited

U.S. PATENT DOCUMENTS

| | | | |
|---|---|---|---|
| 2,446,571 A | 3/1944 | Browne | |
| 2,720,881 A | 10/1955 | Weaver et al. | |
| 2,755,060 A | 7/1956 | Twyman | |
| 3,113,586 A | 12/1963 | Edmark, Jr. | |
| 3,159,175 A | 12/1964 | MacMillan | |
| 3,159,176 A | 12/1964 | Russell et al. | |
| 3,477,438 A * | 11/1969 | Allen et al. | 604/99.03 |
| 3,514,438 A * | 5/1970 | Nelsen et al. | 524/108 |
| 3,525,357 A | 8/1970 | Koreski | |
| 3,621,557 A | 11/1971 | Cushman et al. | |
| 3,669,323 A | 6/1972 | Harker et al. | |
| 3,673,612 A * | 7/1972 | Merrill et al. | 623/2.42 |
| 3,674,183 A | 7/1972 | Venable et al. | |
| 3,710,942 A | 1/1973 | Rosenberg | |
| 3,788,327 A | 1/1974 | Donowitz et al. | |
| 3,811,466 A | 5/1974 | Ohringer | |
| 3,955,594 A * | 5/1976 | Snow | 137/493 |
| 4,072,146 A | 2/1978 | Howes | |
| 4,142,525 A | 3/1979 | Binard et al. | |
| 4,143,853 A * | 3/1979 | Abramson | 251/149.1 |
| 4,244,379 A | 1/1981 | Smith | |
| 4,387,879 A | 6/1983 | Tauschinski | |
| 4,405,316 A | 9/1983 | Mittleman | |
| 4,434,810 A | 3/1984 | Atkinson | |
| 4,447,237 A * | 5/1984 | Frisch et al. | 604/175 |
| 4,468,224 A | 8/1984 | Enzmann et al. | |
| 4,502,502 A | 3/1985 | Krug | |

(Continued)

FOREIGN PATENT DOCUMENTS

DE 20208420 10/2002

(Continued)

OTHER PUBLICATIONS

Asch, "Venous access: options, approaches and issues," Can Assoc. Radiol J., vol. 52, No. 3 pp. 153-164 (2001).

(Continued)

*Primary Examiner* — Theodore Stigell
(74) *Attorney, Agent, or Firm* — Bingham McCutchen LLP

(57) ABSTRACT

A pressure activated valve comprises a valve housing defining a lumen for receiving bodily fluids therein and a flexible membrane disposed in the valve housing. The flexible membrane includes a slit extending therethrough so that the flexible membrane may be moved between an open and a closed configuration based on fluid pressure within the lumen. A nonthrombogenic coating may be formed on fluid contacting surfaces of the flexible membrane.

11 Claims, 3 Drawing Sheets

U.S. PATENT DOCUMENTS

| | | | |
|---|---|---|---|
| 4,524,805 A | 6/1985 | Hoffman | |
| 4,543,087 A | 9/1985 | Sommercorn et al. | |
| 4,552,553 A | 11/1985 | Schulte et al. | |
| 4,610,665 A * | 9/1986 | Matsumoto et al. | 604/167.04 |
| 4,616,768 A | 10/1986 | Flier | |
| 4,673,393 A | 6/1987 | Suzuki et al. | |
| 4,681,572 A | 7/1987 | Tokarz et al. | |
| 4,692,146 A | 9/1987 | Hilger | |
| 4,722,725 A | 2/1988 | Sawyer et al. | |
| 4,790,832 A | 12/1988 | Lopez | |
| 4,798,594 A | 1/1989 | Hillstead | |
| 4,801,297 A | 1/1989 | Mueller | |
| 4,908,028 A | 3/1990 | Colon et al. | |
| 4,944,726 A | 7/1990 | Hilal et al. | |
| 4,946,448 A | 8/1990 | Richmond | |
| 5,000,745 A | 3/1991 | Guest et al. | |
| 5,009,391 A * | 4/1991 | Steigerwald | 251/149.1 |
| 5,030,210 A | 7/1991 | Alchas et al. | |
| 5,084,015 A | 1/1992 | Moriuchi | |
| 5,098,405 A | 3/1992 | Peterson et al. | |
| 5,125,893 A | 6/1992 | Dryden | |
| 5,147,332 A | 9/1992 | Moorehead | |
| 5,149,327 A | 9/1992 | Oshiyama | |
| 5,167,638 A | 12/1992 | Felix et al. | |
| 5,169,393 A | 12/1992 | Moorehead et al. | |
| 5,176,652 A | 1/1993 | Littrell | |
| 5,176,662 A | 1/1993 | Bartholomew et al. | |
| 5,201,722 A | 4/1993 | Moorehead et al. | |
| 5,205,834 A | 4/1993 | Moorehead et al. | |
| 5,249,598 A * | 10/1993 | Schmidt | 137/493.1 |
| 5,254,086 A | 10/1993 | Palmer et al. | |
| 5,324,274 A | 6/1994 | Martin | |
| 5,330,424 A | 7/1994 | Palmer et al. | |
| 5,336,203 A | 8/1994 | Goldhardt et al. | |
| 5,360,407 A | 11/1994 | Leonard et al. | |
| 5,370,624 A | 12/1994 | Edwards et al. | |
| 5,395,352 A | 3/1995 | Penny | |
| 5,396,925 A | 3/1995 | Poli et al. | |
| 5,399,168 A | 3/1995 | Wadsworth et al. | |
| 5,401,255 A | 3/1995 | Sutherland et al. | |
| D357,735 S | 4/1995 | McPhee | |
| 5,405,340 A | 4/1995 | Fageol et al. | |
| 5,411,491 A | 5/1995 | Goldhardt et al. | |
| 5,453,097 A * | 9/1995 | Paradis | 604/247 |
| 5,454,784 A | 10/1995 | Atkinson et al. | |
| 5,469,805 A | 11/1995 | Gibbs et al. | |
| 5,470,305 A | 11/1995 | Arnett et al. | |
| 5,484,420 A | 1/1996 | Russo | |
| 5,542,923 A | 8/1996 | Ensminger et al. | |
| 5,554,136 A | 9/1996 | Luther | |
| 5,562,618 A | 10/1996 | Cai et al. | |
| 5,571,093 A | 11/1996 | Cruz et al. | |
| 5,575,769 A | 11/1996 | Vaillancourt et al. | |
| 5,624,395 A | 4/1997 | Mikhail et al. | |
| 5,637,099 A | 6/1997 | Durdin et al. | |
| 5,667,500 A | 9/1997 | Palmer et al. | |
| 5,707,357 A | 1/1998 | Mikhail et al. | |
| 5,743,873 A | 4/1998 | Cai et al. | |
| 5,743,884 A | 4/1998 | Hasson et al. | |
| 5,743,894 A | 4/1998 | Swisher | |
| 5,752,938 A | 5/1998 | Flatland et al. | |
| 5,803,078 A | 9/1998 | Brauner | |
| 5,807,349 A | 9/1998 | Person et al. | |
| 5,843,044 A | 12/1998 | Moorehead | |
| 5,853,397 A | 12/1998 | Shemesh et al. | |
| 5,865,308 A | 2/1999 | Qin et al. | |
| 5,944,698 A | 8/1999 | Fischer et al. | |
| 5,984,902 A | 11/1999 | Moorehead | |
| 6,033,393 A | 3/2000 | Balbierz et al. | |
| 6,045,734 A | 4/2000 | Luther et al. | |
| 6,050,934 A | 4/2000 | Mikhail et al. | |
| 6,056,717 A | 5/2000 | Finch et al. | |
| 6,062,244 A | 5/2000 | Arkans | |
| 6,092,551 A | 7/2000 | Bennett | |
| 6,099,505 A | 8/2000 | Ryan et al. | |
| 6,120,483 A | 9/2000 | Davey et al. | |
| 6,152,909 A | 11/2000 | Bagaoisan et al. | |
| 6,210,366 B1 | 4/2001 | Sanfilippo | |
| 6,227,200 B1 | 5/2001 | Crump et al. | |
| 6,270,489 B1 | 8/2001 | Wise et al. | |
| 6,306,124 B1 | 10/2001 | Jones et al. | |
| 6,364,861 B1 | 4/2002 | Feith et al. | |
| 6,364,867 B2 | 4/2002 | Wise et al. | |
| 6,375,637 B1 | 4/2002 | Campbell et al. | |
| 6,436,077 B1 | 8/2002 | Davey et al. | |
| 6,442,415 B1 | 8/2002 | Bis et al. | |
| 6,446,671 B2 | 9/2002 | Armenia et al. | |
| 6,508,791 B1 | 1/2003 | Guerrero | |
| 6,551,270 B1 | 4/2003 | Bimbo et al. | |
| 6,610,031 B1 * | 8/2003 | Chin | 604/167.04 |
| 6,726,063 B2 | 4/2004 | Stull et al. | |
| 6,786,884 B1 | 9/2004 | DeCant et al. | |
| 6,874,999 B2 | 4/2005 | Dai et al. | |
| 6,953,450 B2 | 10/2005 | Baldwin et al. | |
| 6,994,314 B2 | 2/2006 | Garnier et al. | |
| 7,081,106 B1 | 7/2006 | Guo et al. | |
| 7,252,652 B2 | 8/2007 | Moorehead et al. | |
| 7,291,133 B1 | 11/2007 | Kindler et al. | |
| 7,316,655 B2 | 1/2008 | Garibotto et al. | |
| 7,435,236 B2 | 10/2008 | Weaver et al. | |
| 7,601,141 B2 | 10/2009 | Dikeman et al. | |
| 7,637,893 B2 | 12/2009 | Christensen et al. | |
| 7,758,541 B2 | 7/2010 | Wallace et al. | |
| 2001/0023333 A1 | 9/2001 | Wisse et al. | |
| 2001/0037079 A1 | 11/2001 | Burbank et al. | |
| 2002/0010425 A1 | 1/2002 | Guo et al. | |
| 2002/0016584 A1 | 2/2002 | Wise et al. | |
| 2002/0121530 A1 | 9/2002 | Socier | |
| 2002/0156430 A1 | 10/2002 | Haarala et al. | |
| 2002/0165492 A1 | 11/2002 | Davey et al. | |
| 2002/0193752 A1 | 12/2002 | Lynn | |
| 2003/0122095 A1 | 7/2003 | Wilson et al. | |
| 2004/0034324 A1 | 2/2004 | Seese et al. | |
| 2004/0064128 A1 | 4/2004 | Raijman et al. | |
| 2004/0102738 A1 | 5/2004 | Dikeman | |
| 2004/0108479 A1 | 6/2004 | Garnier et al. | |
| 2004/0186444 A1 | 9/2004 | Daly et al. | |
| 2004/0193119 A1 | 9/2004 | Canaud et al. | |
| 2004/0210194 A1 | 10/2004 | Bonnette et al. | |
| 2004/0267185 A1 * | 12/2004 | Weaver et al. | 604/6.16 |
| 2005/0010176 A1 * | 1/2005 | Dikeman et al. | 604/247 |
| 2005/0027261 A1 | 2/2005 | Weaver et al. | |
| 2005/0043703 A1 | 2/2005 | Nordgren | |
| 2005/0049555 A1 * | 3/2005 | Moorehead et al. | 604/122 |
| 2005/0149116 A1 | 7/2005 | Edwards et al. | |
| 2005/0171490 A1 | 8/2005 | Weaver et al. | |
| 2005/0171510 A1 | 8/2005 | DiCarlo et al. | |
| 2005/0283122 A1 | 12/2005 | Nordgren | |
| 2006/0129092 A1 | 6/2006 | Hanlon et al. | |
| 2006/0135949 A1 | 6/2006 | Rome et al. | |
| 2006/0149211 A1 | 7/2006 | Simpson et al. | |
| 2007/0161940 A1 | 7/2007 | Blanchard et al. | |
| 2007/0161970 A1 | 7/2007 | Spohn et al. | |
| 2007/0276313 A1 | 11/2007 | Moorehead et al. | |
| 2008/0108956 A1 | 5/2008 | Lynn et al. | |
| 2009/0292252 A1 | 11/2009 | Lareau et al. | |

FOREIGN PATENT DOCUMENTS

| | | |
|---|---|---|
| EP | 0128525 | 12/1984 |
| EP | 0337617 | 10/1989 |
| EP | 0366814 | 5/1990 |
| EP | 0474069 | 3/1992 |
| EP | 0864336 | 9/1998 |
| EP | 0930082 | 7/1999 |
| EP | 1016431 | 7/2000 |
| FR | 2508008 | 12/1982 |
| FR | 2718969 | 10/1995 |
| GB | 966137 | 8/1964 |
| GB | 2102398 | 2/1983 |
| JP | 59133877 | 8/1984 |
| JP | 63255057 | 10/1988 |
| JP | 9038197 | 2/1997 |
| WO | WO-89/02764 | 4/1989 |
| WO | WO-91/12838 | 9/1991 |
| WO | 92/06732 | 4/1992 |
| WO | 95/16480 | 6/1995 |
| WO | WO-96/17190 | 6/1996 |

| WO | WO-96/23158 | 8/1996 |
| WO | WO-96/41649 | 12/1996 |
| WO | 97/23255 | 7/1997 |
| WO | 97/26931 | 7/1997 |
| WO | WO-98/22178 | 5/1998 |
| WO | 99/42166 | 8/1999 |
| WO | WO-00/06230 | 2/2000 |
| WO | 00/44419 | 8/2000 |
| WO | 03/084832 | 10/2003 |
| WO | 2005/023355 | 3/2005 |
| WO | WO-2008/089985 | 7/2008 |

OTHER PUBLICATIONS

Herts et al., "Power injection of contrast media using central venous catheters: feasibility, safety, and efficacy," AJR Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatrict CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahous et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

International Search Report and Written Opinion mailed Jul. 20, 2005 for International Application No. PCT/US2005/000760 (13 pages).

International Preliminary Report on Patentability mailed Jul. 31, 2006 for International Application No. PCT/US2005/000760 (8 pages).

* cited by examiner

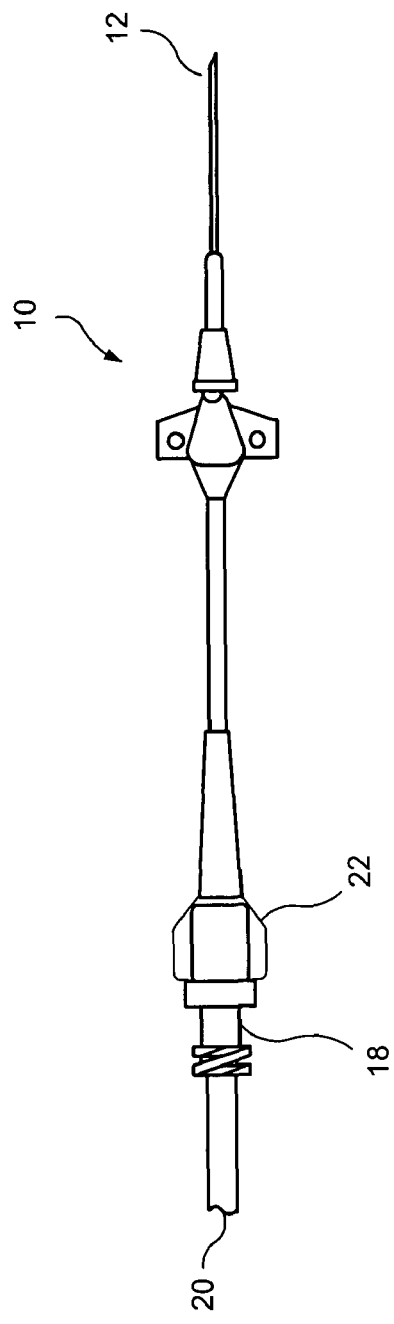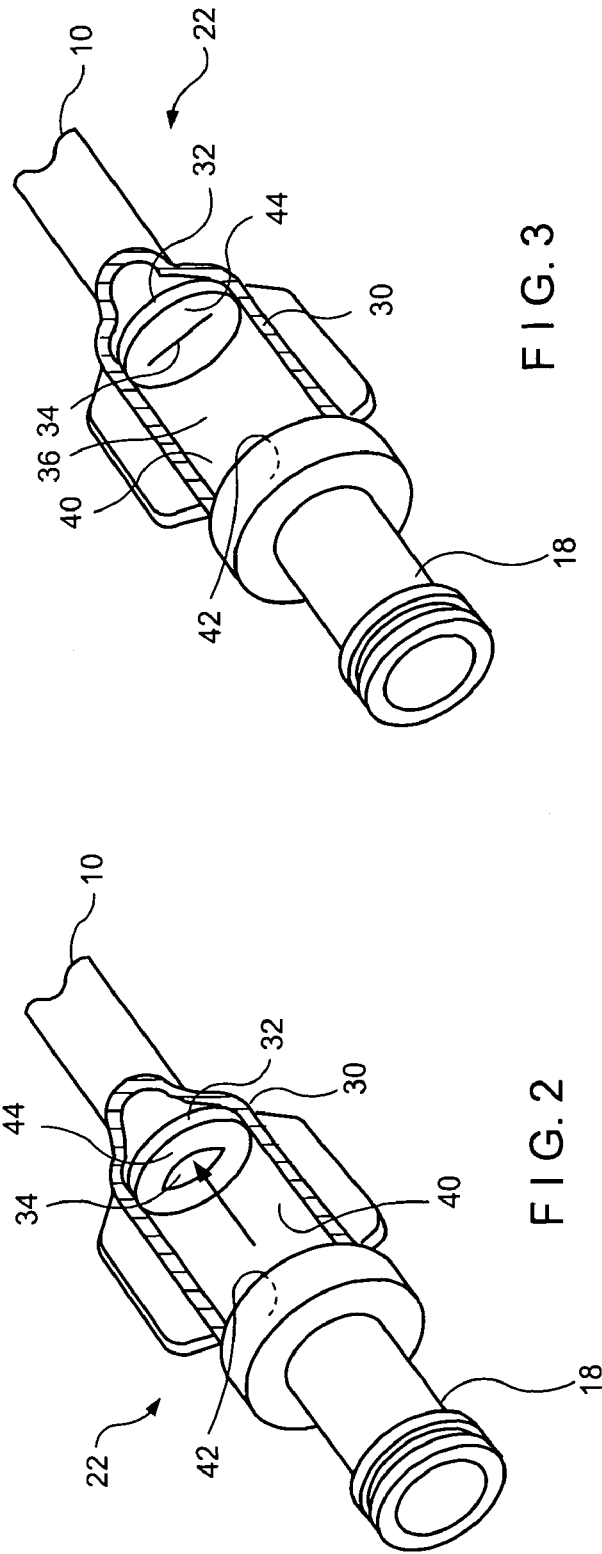

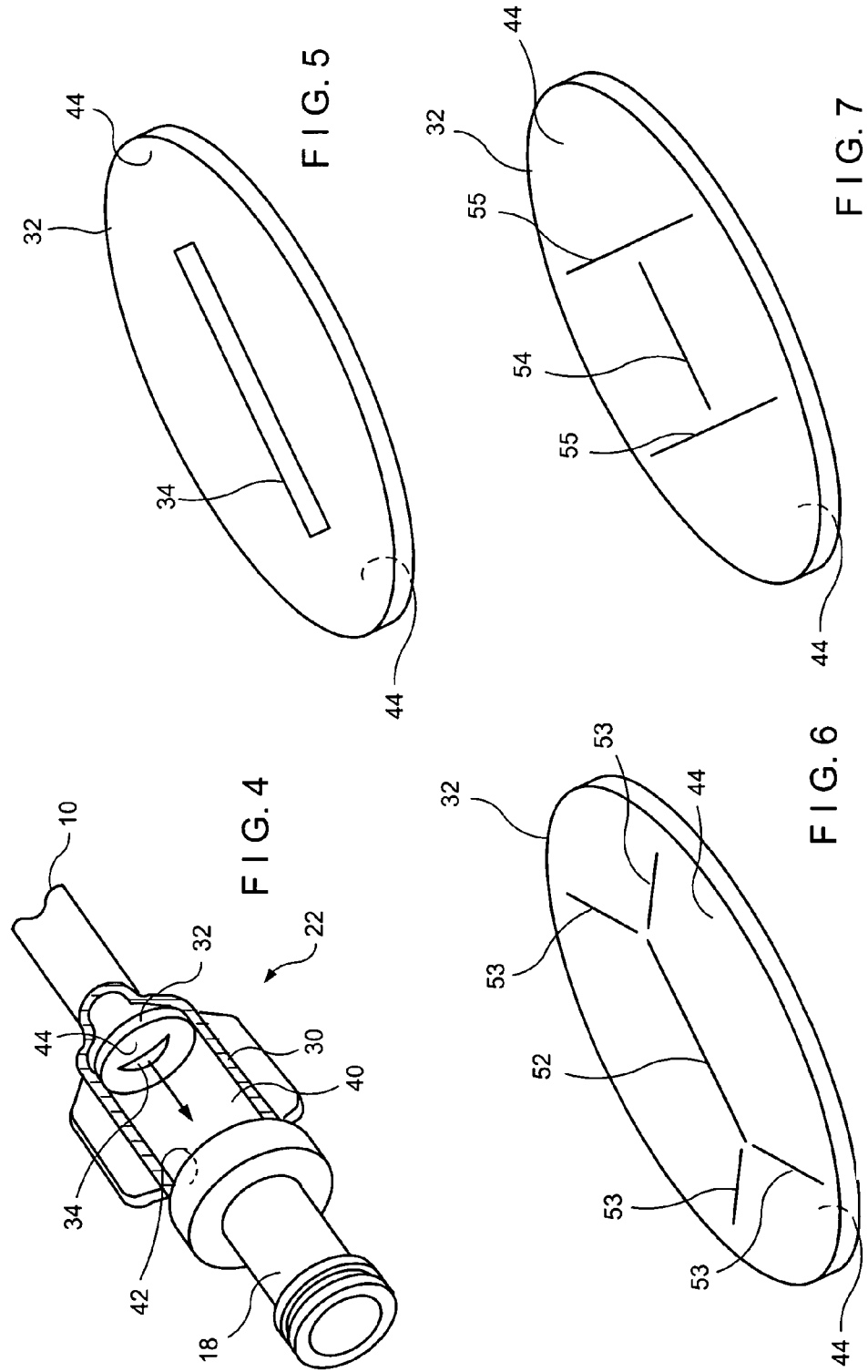

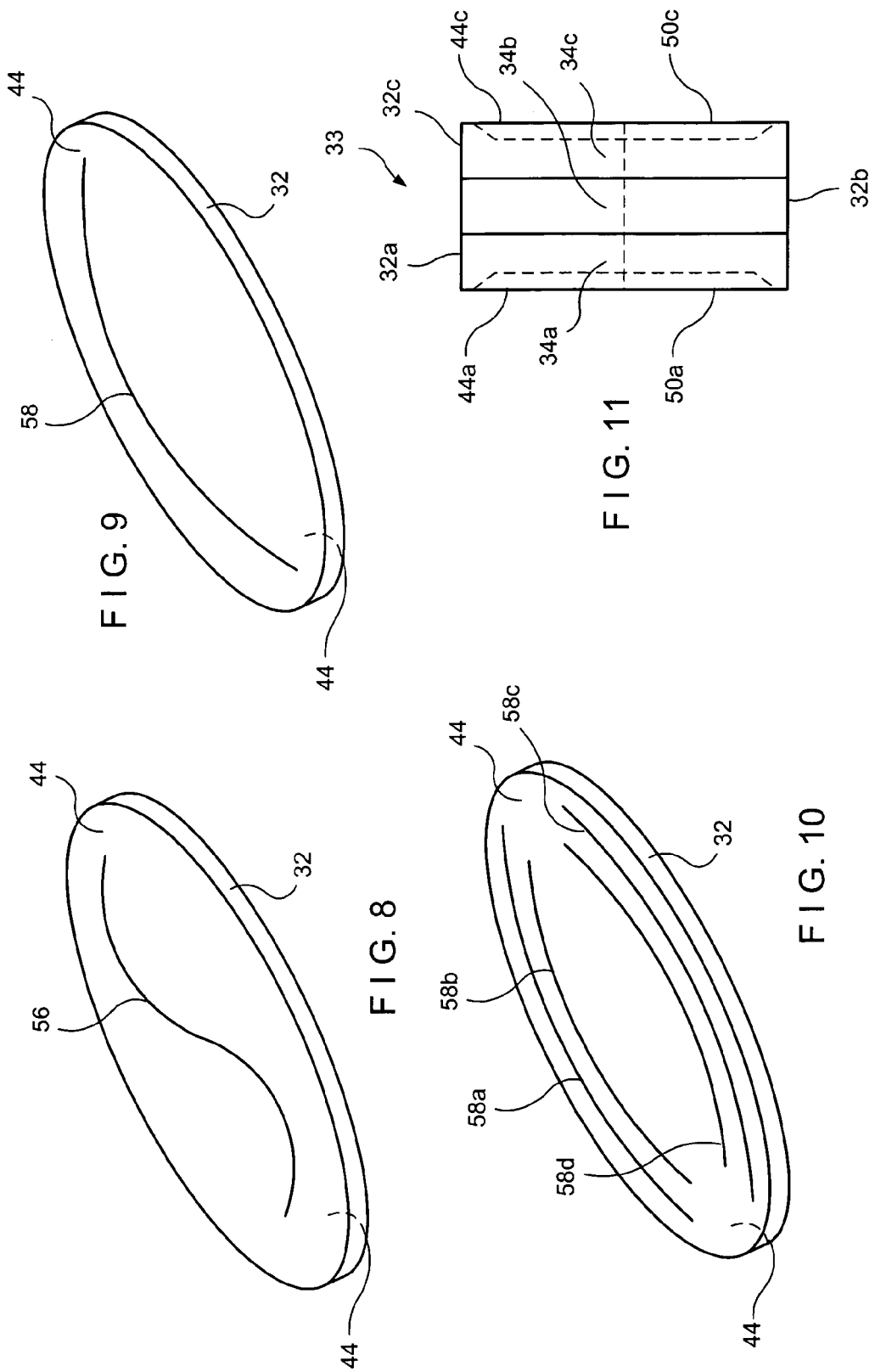

PRESSURE ACTIVATED SAFETY VALVE WITH ANTI-ADHERENT COATING

The present application incorporates by reference entire disclosure of (1) U.S. application Ser. No. 10/768,565 entitled "Pressure Activated Safety Valve With High Flow Slit" filed on Jan. 29, 2004 naming Karla Weaver and Paul DiCarlo as inventors; (2) U.S. application Ser. No. 10/768,629 entitled "Stacked Membrane For Pressure Actuated Valve" filed on Jan. 29, 2004 naming Karla Weaver and Paul DiCarlo as inventors; (3) U.S. application No. 10/768,855 entitled "Pressure Actuated Safety Valve With Spiral Flow Membrane" filed on Jan. 29, 2004 naming Karla Weaver and Paul DiCarlo as inventors; and (4) U.S. application Ser. No. 10/768,479 entitled "Dual Well Port Device" filed on Jan. 29, 2004 naming Katie Daly, Kristian DiMatteo and Eric Houde as inventors.

BACKGROUND OF THE INVENTION

Many medical procedures require repeated and prolonged access to a patient's vascular system. For example, during dialysis treatment blood may be removed from the body for external filtering and purification, to make up for the inability of the patient's kidneys to carry out that function. In this process, the patient's venous blood is extracted, processed in a dialysis machine and returned to the patient. The dialysis machine purifies the blood by diffusing harmful compounds through membranes, and may add to the blood therapeutic agents, nutrients etc., as required before returning it to the patient's body. Typically the blood is extracted from a source vein (e.g., the vena cava) through a catheter sutured to the skin with a distal needle of the catheter penetrating the source vein.

It is impractical and dangerous to insert and remove the catheter for each dialysis session. Thus, the needle and catheter are generally implanted semi permanently with a distal portion of the assembly remaining within the patient in contact with the vascular system while a proximal portion of the catheter remains external to the patient's body. The proximal end is sealed after each dialysis session has been completed to prevent blood loss and infections. However, even small amounts of blood oozing into the proximal end of the catheter may be dangerous as thrombi can form therein due to coagulation. These thrombi may then be introduced into the patient's vascular system when blood flows from the dialysis machine through the catheter in a later session.

A common method of sealing the catheter after a dialysis session is to shut the catheter with a simple clamp. This method is often unsatisfactory because the repeated application of the clamp may weaken the walls of the catheter due to the stress placed on the walls at a single point. In addition, the pinched area of the catheter may not be completely sealed allowing air to enter the catheter which may coagulate any blood present within the catheter. Alternatively, valves have been used at the opening of the catheter in an attempt to prevent leaking through the catheter when the dialysis machine is disconnected. However, the unreliability of conventional valves has rendered them unsatisfactory for extended use.

SUMMARY OF THE INVENTION

In one aspect, the present invention is directed to a pressure activated valve comprising a valve housing defining a lumen for receiving bodily fluids therein and a flexible membrane disposed in the valve housing. The flexible membrane includes a slit extending therethrough so that the flexible membrane may be moved between an open and a closed configuration based on fluid pressure within the lumen. A nonthrombogenic coating is formed on fluid contacting surfaces of the flexible membrane.

BRIEF DESCRIPTION OF THE DRAWINGS

FIG. 1 is a diagram showing a central line catheter according to an embodiment of the present invention;

FIG. 2 is a diagram showing a cutaway view of a pressure activated valve according to an embodiment of the present invention, in open configuration when a fluid is being introduced;

FIG. 3 is a diagram showing a cutaway view of the pressure activated valve according to an embodiment of the present invention, in closed configuration;

FIG. 4 is a diagram showing a cutaway view of the pressure activated valve according to an embodiment of the present invention, in open configuration when the fluid is being withdrawn;

FIG. 5 is a diagram showing a silicone disk forming an openable element of a pressure activated valve according to an embodiment of the present invention;

FIG. 6 is a diagram showing a silicone disk having a Y-shaped slit forming an openable element of a pressure activated valve according to an embodiment of the present invention;

FIG. 7 is a diagram showing a silicone disk having a H-shaped slit forming an openable element of a pressure activated valve according to an embodiment of the present invention;

FIG. 8 is a diagram showing a silicone disk having a S-shaped slit forming an openable element of a pressure activated valve according to an embodiment of the present invention;

FIG. 9 is a diagram showing a silicone disk having a radially shaped slit forming an openable element of a pressure activated valve according to an embodiment of the present invention;

FIG. 10 is a diagram showing a silicone disk having a plurality of slits forming an openable element of a pressure activated valve according to an embodiment of the present invention; and FIG. 11 is a diagram showing three silicone disks forming an openable element of a pressure activated valve according to an embodiment of the present invention.

DETAILED DESCRIPTION

The present invention may be further understood with reference to the following description and the appended drawings, wherein like elements are referred to with the same reference numerals. The present invention is related to medical devices used to access the vascular system of a patient, and in particular to central line catheters used for chronic access to a vein or artery.

Semi-permanently placed catheters may be useful for a variety of medical procedures which require repeated access to a patient's vascular system in addition to the dialysis treatments mentioned above. For example, chemotherapy infusions may be repeated several times a week for extended periods of time. For safety reasons, as well as to improve the comfort of the patient, injections of these therapeutic agents may be better carried out with an implantable, semi-permanent vascular access catheter. Many other conditions that require chronic venous supply of therapeutic agents, nutrients, blood products or other fluids to the patient may also benefit from implantable access catheters, to avoid repeated insertion of a needle into the patient's blood vessels. Thus, although the following description focuses on dialysis, those skilled in the art will understand that the invention may be used in conjunction with any of a wide variety of procedures which require long term implantation of catheters within the body.

Examples of such implantable catheters include those manufactured by Vaxcel™, such as the Chronic Dialysis Catheter and the Implantable Vascular Access System. These devices typically are inserted under the patient's skin, and have a distal end which includes a needle used to enter a blood vessel. The devices also have a proximal end extending outside the body for connection with an outside line. These semi-permanent catheters may be sutured to the patient's skin to maintain them in place while the patient goes about his or her normal occupations.

FIG. 1 shows an exemplary catheter such as, for example, the Vaxcel™ Chronic Dialysis Catheter. The catheter 10 has a distal end 12 that is insertable into a patient's vein, and which remains within the patient's body for the life of the catheter 10. The distal end 12 includes a needle (not shown) that pierces the vein of the patient to reach the flow of blood. During dialysis, blood from the patient is removed through the catheter 10, and is purified by a dialysis machine (not shown) which is connected to a hub 18 of the catheter 10 via an external line 20. The catheter 10 may include two or more lumens with a first one of the lumens being used to remove blood from the blood vessel and a second one of the lumens being used to reintroduced treated blood and/or therapeutic agents into the blood vessel. As described above, in addition to dialysis, devices similar to the catheter 10 may be used to access a patient's vascular system for other types of treatment, for example to infuse chemotherapy agents or other medications, to supply food and to remove blood samples.

When disconnected from the dialysis machine, the catheter 10 remains within the patient, connected to the patient's vascular system. Thus, it is important to securely seal the hub 18 to prevent fluids from escaping therefrom and contaminants from entering the patient's body. For example, although the proximal end of the catheter 10 may be clamped to close it off, if an effective seal is not obtained, the patient runs a serious of infection as well as risks of embolisms due to air entering the blood stream and venous thrombosis due to coagulation of blood in and near the catheter. In addition, leakage from an improperly sealed catheter may expose attending medical staff to a risk of infection by blood borne pathogens. Thus a mechanism is necessary to ensure that the catheter 10 is sealed when not in use.

Conventional clamps or clips have been used to seal such catheters 10 between medical sessions. However, as the sealing forces repeatedly applied by these clips is exerted on a small portion of the surface area of the catheter 10, damage to the wall of the catheter 10 at this portion can significantly reduce the effective life of the catheter 10. It is also desired to improve the resistance of a sealing mechanism for the catheter 10 to forces applied during activities of the patient, so that the sealing mechanism will remain effective without restricting the activity of the patient. Finally, it is desired to minimize the bulk of the sealing mechanism to enhance patient comfort.

An alternative to clamping or clipping the catheter 10 is to include self sealing valves near the entrance of the flow passages of the catheter, to seal those passages when not in use. For example, the hub 18 may house one or more valves 22 which are designed to seal the lumen(s) of the catheter 10 under certain conditions, and to allow passage of fluid therethrough under other conditions. In an exemplary case applicable to a dialysis catheter, the system of valves may seal the catheter 10 when it is not connected to an operating dialysis machine, and may allow both an outflow of non-purified blood and an inflow of purified blood to the patient when an operating dialysis machine is connected thereto. These valves 22 thus selectively allow flow into or out of the patient depending on whether they are placed in fluid contact with the inflow or outflow portions of the dialysis catheter.

Pressure activated safety valves (PASV's) are one type of flow control device that has been used to seal vascular catheters when not in use. These valves open when subject to flow pressure of at least a pre-determined value and remain closed when subject to pressures below the pre-determined value. In the exemplary case of a PASV used in a dialysis catheter, the valve is preferably designed so that the pre-determined pressure substantially exceeds a pressure to which the valve would be subjected from the vascular system or due to patient activity and may correspond to a pressure approximating a lower level of the pressures to which the valve would be subjected by an operating dialysis machine. Thus, when no dialysis machine is connected to the catheter, the pressure in the lumen is insufficient to open the PASV, and the catheter remains sealed.

FIGS. 2-4 show a more detailed view of a PASV 22, shown in a cutaway drawing depicting three flow conditions in a single lumen catheter 10 which handles blood flow from and to the patient's vascular system. FIG. 2 shows PASV 22 as a fluid is being introduced into the catheter 10 from the hub 18. FIG. 3 shows the valve is closed and no flow is present, and FIG. 4 shows PASV 22 as fluid is being removed from the catheter 10 to the hub 18, and. In the context of a dialysis catheter, FIGS. 2 and 4, respectively, correspond to blood being returned to and withdrawn from a patient while FIG. 3 corresponds to a condition in which no dialysis treatment is being performed and the PASV 22 is in the sealed configuration. According to one exemplary embodiment of the present invention, the PASV 22 comprises a valve housing 30 forming a body of the device and a slitted membrane 32 disposed within the housing 30. The hub 18 may define the valve housing 30 or, alternatively, the housing 30 and the hub 18 may be separate units. The housing 30 defines a flow chamber 36 through which the fluid flows into and out of the catheter 10. The exemplary flow chamber 36 is substantially cylindrical. However, those skilled in the art will understand that, for different applications, the flow chamber 36 may be of any shape suitable for the efficient flow of a fluid therethrough.

The slitted membrane 32 may be disposed at any point within the catheter 10. However, for purposes of illustration, the membrane 32 is described as positioned at one end of the flow chamber 36 positioned to selectively impede the passage of fluid therethough. As shown more clearly in FIG. 5, a slit 34 is formed in the membrane 32 so that under pre-determined conditions the slit 34 opens to allow fluid flow through the membrane 32. When the pre-determined conditions are not present, the slit 34 remains closed to prevent fluid flow therethrough. For example, as described above, the slitted membrane 32 may be constructed so that the slit 34 opens when subject to a flow pressure of at least a predetermined magnitude, but remains securely closed at other times. According to embodiments of the invention, the PASV 22 includes a slitted membrane 32 that is movable to an open configuration in response to a predetermined flow pressure, and is biased into the closed configuration at all times while the flow pressure remains below the predetermined flow pressure. The slitted membrane 32 may be formed, for example, from silicone or from any of a variety of polymer compounds.

FIGS. 2-4 show one exemplary embodiment of a pressure activated valve according to the present invention. Those of skill in the art will understand that different configurations of the housing 30, the slitted membrane 32 and the slit 34 may be used without departing from the invention. For example, as shown in FIGS. 6-9 and discussed in more detail below, one or more differently shaped slits of various sizes may be employed, to tailor the flow through the membrane 32 and to vary the pressure required to open the slit 34. Furthermore, the membrane 32 may have a different shape and may be located at any place within the housing 30. The housing 30 may also define a flow chamber 36 having a different shape than the substantially cylindrical chamber shown in FIGS. 2-4 with the shape of the membrane 32 being modified to suit the cross-section of the area at which it is to be mounted. For example, the membranes of FIGS. 5-10 are depicted as substantially elliptical. However, those skilled in the art will understand that a flow chamber and membranes of any shape may be employed to achieve desired flow characteristics through the catheter 10.

FIG. 6 shows a membrane 32 that is substantially elliptical with a first slit 52 extending along a major axis thereof. In addition, a pair of slits 53 is disposed at each end of the slit 52 with the slits 53 of each pair extending away from the slit 52 at an angle relative thereto along lines which converge near the end points of the slit 52. The ends of the slits 53 may be separated from the corresponding end of the slit 52 by a distance selected to enhance the structural integrity of the membrane 32 and to increase the threshold pressure to a desired level. However, those skilled in the art will understand that the slits 53 may intersect the slit 52 in order to achieve desired flow characteristics so long as the strength of the membrane 32 is maintained at a level sufficient to withstand the conditions to which it is to be subjected.

FIG. 7 shows a substantially elliptical slitted membrane 32 with an H-shaped configuration of slits 54, 55. The slit 54 extends substantially along a major axis of the membrane 32 with the slits 55 extending substantially perpendicular thereto and separated from ends of the slit 54. As described above, the slits 54 and 55 may intersect if necessary to achieve the desired flow characteristics of the membrane 32 so long as the structural integrity of the membrane 32 is not compromised. Of course, those skilled in the art will understand that the shape of the membrane 32 does not influence the arrangement of the slits formed therein except to the extent that ends of the slits may need to be separated from an outer edge of the membrane 32 by a distance sufficient to maintain the strength of the membrane 32.

FIG. 8 shows another embodiment of a slitted membrane 32 with a substantially S-shaped slit 56 which preferably extends substantially along a center line thereof. For example, if the slitted membrane 32 is substantially elliptical then the S-shaped slit will oscillate about the major axis thereof. FIG. 9 shows a membrane 32 including a curved slit 58. The curved slit 58 may have any shape and radius of curvature necessary to achieve desired flow characteristics of the membrane 32.

Furthermore, the membrane 32 may include a plurality of curved slits 58 as shown in FIG. 10. FIG. 10 shows a slitted membrane 32 including four curved slits 58a-58d with slits 58a and 58b positioned on one side of a major axis of the membrane 32 and slits 58c and 58d located on an opposite side thereof. Those skilled in the art will understand that FIG. 10 shows only one an exemplary embodiment of a slitted membrane 32 including a plurality of slits 58 and that a membrane 32 according to the present invention may include any number of slits 58, which may be of any shape and/or size depending on the flow control requirements of the PASV 22.

FIG. 11 shows a membrane 33 formed of three slitted membranes 32a-32c stacked on one another. The membrane 33 may be positioned in the flow chamber 36 in a manner substantially similar to that described above for the membranes 32 in order to provide flow control in the PASV 22. Stacking multiple membranes 32a-32c provides greater flexibility and tensile strength to the PASV 22 and any number of membranes may be stacked to form such a membrane 33. Those skilled in the art will understand that the slitted membrane 32a has a first slit 34a formed therein in any manner as described above and the slitted membrane 32b has a first slit 34b formed therein while the slitted membrane 32c has a first slit 34c formed therein. Each of the slitted membranes 32a-32c may have more slits formed therein and these additional slits will preferably align with one another, so that continuous flow paths are formed through the membrane 33. In addition, these slits 34a-34c may be of different shapes and do not have to match the size and shape of adjacent slits. For example, the slit(s) 34a in the membrane 32a may be substantially S-shaped, while the slit 34b in the membrane 32b may be substantially linear. In addition, one or more of the membranes 32a-32c may have multiple slits as described above. Furthermore, the slitted membranes 32a-32c do not have to be made of the same material nor do the membranes 32a-32c need to have uniform dimensions (e.g., thickness). This versatility allows PASV 22 to be designed around specific flow control needs. While FIG. 11 shows a membrane 33 comprising three slitted membranes 32a-32c, one skilled in the art will understand that any number of slitted membranes may be used, depending on the flow control requirements of the PASV 22.

Furthermore, the slitted membranes 32a and 32c that form outer surfaces of the membrane 33 may be beveled by creating grooves 50a and 50c on surfaces 44a and 44c, respectively to direct fluid flow toward the slits 34a-34c which are generally centrally located. In the case of single membranes 32, creating grooves or reducing the thickness of portions thereof may undesirably reduce the strength thereof. However, the multiple slitted membranes 32a-32c of the membrane 33 provide additional strength despite the reduced thickness portions resulting from the reduced thickness of the membranes 32a and 32c.

Whenever a foreign object is placed in contact with the flow of blood, and to a certain extent with other bodily fluids, there is a possibility that an occlusion will be formed due to the deposition of cells present in the blood or other bodily fluid which may present health risks well known to those skilled in the art. For example, in the case of a PASV 22 in a lumen fluidly coupled to a blood vessel, a fibrin occlusion or clot may form on a surface of the PASV 22 and/or on the face of a slitted membrane 32 thereof.

The materials used to construct modern medical devices such as the PASV 22 and the slitted membrane 32 are usually synthetic. Thus, when these materials come in contact with blood, various reactions such as platelet attachment and platelet activation may be activated that eventually progress to the production of fibrin and to the formation of a clot. The flow pattern within a valve such as PASV 22 may also to promote the formation of clots. That is, as the blood flowing through the PASV 22 and across the slit is slowed down and redirected by the obstruction presented by the slitted membrane 32 areas of flow recirculation and stagnation may be formed within the PASV 22. These flow conditions may promote the formation of thrombi (clots), which may remain within the PASV 22 or which may enter the vascular system.

Coagulation of blood in catheters has been treated by administering to the patient systemic anticoagulants, such as injectable heparin and warfarin. However, this approach risks complications due to the possible intolerance of the patient to those drugs. In addition, in procedures when the devices remain in the patient's body for extended periods of time, continuous administration of anti coagulant medications may not be practical.

According to embodiments of the present invention, a PASV 22 is described which minimizes the formation of clots and/or occlusions in and around the PASV 22. The catheter 10 according to the present invention includes a nonthrombogenic coating over surfaces of the device in the vicinity of the PASV 22 as well as on the surfaces of the PASV 22 itself. In particular, a nonthrombogenic coating is applied to inner surfaces of the housing 30 including the lumen walls 40 and end walls 42 thereof. In addition, a flexible nonthrombogenic coating may be applied to the surfaces 44 of the slitted membrane 32 that contact blood or other bodily fluids.

Different nonthrombogenic compounds may be used to coat the surfaces of interest. For example, heparin, hydrogel alone or combined with heparin, and phosphorylcholine may be processed to form a coating on the PASV 22 and the adjacent inner surfaces of the housing 30. As would be understood by those skilled in the art, hydrogels are compounds used to dress incisions and to coat medical devices to facilitate their insertion into a body cavity. In addition to their lubricating properties, hydrogels also exhibit anticoagulant properties. It has been observed that a coating of hydrogel disposed on a medical device results in a significant reduction in the attachment and activation of platelets to the device's surfaces. This may be due to the low friction surface presented by the coating. Accordingly, the surface concentration of platelets may be lower on the surfaces of a PASV valve coated with hydrogel as compared to an untreated valve.

Heparin which has typically been used as an anti-coagulant agent injected directly into a patient's blood stream may also be used to form a biologically active coating on the surfaces of the PASV 22 which contact blood or on the surfaces of the housing 30 adjacent thereto. This type of biologically active coating may be more effective than a coating such as hydrogel, which simply reduces mechanical friction between the device's surfaces and the blood molecules as heparin prevents platelets from adhering to surfaces by interfering with the activation of various enzymes that otherwise result in the formation of fibrin and in the subsequent clotting of blood.

Similarly to heparin, coatings containing phosphorylcholine can be applied to medical devices such as the valves of a catheter to form a biologically active coating which reduces the formation of surface clots. Phosphorylcholine inhibits the adsorption of proteins and reduces adhesion and activation of platelets to the surface of synthetic materials. It is thus also an effective agent which may be applied to devices where it is critical to minimize the formation of clots. Additional biologically active compounds may be used to form a coating on the surfaces of valve housing 30 and slitted membrane 32 which are in contact with blood.

In an exemplary embodiment, the coatings applied to the surfaces 44 of the slitted membrane 32 are preferably flexible and are designed to adhere thereto and remain in place on these surfaces. Those skilled in the art will understand that, if the housing 30 is made flexible, the coatings applied to the inner surfaces 40, 42 of the lumen of the housing 30 may also require a certain degree of flexibility to account for bending of the housing 30 during use and during activity of the patient. However, the coating on the surfaces 44 of the slitted membrane 32 will be subject to more significant stress and strain as the slitted membrane 32 is repeatedly moved between the open and closed configurations during use. In any case, for both the surfaces 40, 42 and 44, a coating including a polymer which is able to retain a therapeutic compound therein may be used. The ability of the nonthrombogenic coating to remain in place without flaking, cracking or otherwise losing its integrity is important, since any loose pieces of the coating may travel into the vascular system. In addition, damage to the coating could expose the valve's surfaces to the flow of blood, and increase the probability that blood clots will form thereon. Those skilled in the art will understand that known methods may be used to form a flexible coating on components of the pressure activated PASV 22, so that the coating retains its flexibility and integrity over the life of the valve.

The present invention has been described with reference to specific embodiments, more specifically to a pressure activated safety valve used in a dialysis catheter. However, other embodiments may be devised that are applicable to other medical devices, without departing from the scope of the invention. Accordingly, various modifications and changes may be made to the embodiments without departing from the broadest spirit and scope of the present invention as set forth in the claims that follow. The specification and drawings are accordingly to be regarded in an illustrative rather than restrictive sense.

What is claimed is:

1. A pressure activated valve comprising:
a valve housing defining a lumen for receiving bodily fluids therein;
a flexible member disposed in the valve housing, the flexible member comprising a plurality of peripheral flexible membranes stacked on opposing sides of a central flexible membrane, each of the flexible membranes including at least one slit extending therethrough so that each flexible membrane may be moved between an open and a closed configuration based on fluid pressure within the lumen, wherein when all of the flexible membranes are moved to an open position, the flexible member is open to permit fluid flow through the housing; and
a nonthrombogenic coating formed on fluid contacting surfaces of the flexible member,
wherein each of said peripheral flexible membranes includes a beveled surface for directing fluid toward the slits.

2. The valve according to claim 1, wherein the nonthrombogenic coating includes a material which comprises at least one of heparin and phosphorylcholine.

3. The valve according to claim 1, wherein one of a proximally outward and a distally outward face of the flexible membrane includes a fluid directing recess formed therein to direct fluid flow toward the slits of the flexible membranes.

4. The valve according to claim 1, wherein the nonthrombogenic coating is a flexible polymeric coating.

5. The valve according to claim 1, wherein the nonthrombogenic coating includes a material which prevents the formation of blood clots.

6. The valve according to claim 1, wherein the nonthrombogenic coating is a coating comprising at least one of heparin and phosphorylcholine.

7. The valve according to claim 1, wherein said flexible membranes are formed of silicone.

8. The valve according to claim 1, further comprising a second nonthrombogenic coating on bodily-fluid-contacting surfaces of the lumen.

9. The valve according to claim 1, wherein at least one of said at least one slits is linear.

10. The valve according to claim 1, wherein at least one of said at least one slits is curved.

11. The valve according to claim 1, wherein each of said flexible membranes is characterized by a minimum thickness, the minimum thickness of said peripheral flexible membranes being less than the minimum thickness of said central flexible membrane.

* * * * *